(12) United States Patent
Costa Balanzat et al.

(10) Patent No.: US 8,205,506 B2
(45) Date of Patent: Jun. 26, 2012

(54) DEVICE FOR FIXING OF A PRISMATIC MECHANICAL TEST PIECE, METHOD OF UTILIZATION THEREOF AND USES

(75) Inventors: Josep Costa Balanzat, Madrid (ES); Silvia Lazcano Ureña, Madrid (ES); Gloria Santacruz Rodriguez, Madrid (ES); Elio Pajares Bretones, Madrid (ES); Jordi Renart Canalias, Madrid (ES); Norbert Blanco Villaverde, Madrid (ES)

(73) Assignee: Airbus Operations, S.L., Getafe (Madrid) (ES)

( * ) Notice: Subject to any disclaimer, the term of this patent is extended or adjusted under 35 U.S.C. 154(b) by 201 days.

(21) Appl. No.: 12/232,871

(22) Filed: Sep. 25, 2008

(65) Prior Publication Data

US 2009/0241682 A1    Oct. 1, 2009

(30) Foreign Application Priority Data

Mar. 26, 2008    (ES) .................................. 200800842

(51) Int. Cl.
*G01N 3/02*    (2006.01)
(52) U.S. Cl. .......................................................... 73/860
(58) Field of Classification Search ...................... 73/860
See application file for complete search history.

(56) References Cited

U.S. PATENT DOCUMENTS

| | | | | |
|---|---|---|---|---|
| 3,060,813 A | * | 10/1962 | Zwick | 409/235 |
| 3,430,525 A | * | 3/1969 | Powers et al. | 408/72 R |
| 3,750,295 A | * | 8/1973 | Nordmann et al. | 33/548 |
| 3,954,005 A | * | 5/1976 | Edwards | 73/833 |
| 4,192,194 A | * | 3/1980 | Holt | 73/794 |
| 4,941,359 A | * | 7/1990 | Quinn et al. | 73/851 |
| 5,172,895 A | * | 12/1992 | Klimach | 269/41 |
| 5,357,786 A | * | 10/1994 | Lung et al. | 73/81 |
| 5,431,062 A | * | 7/1995 | Baratta | 73/856 |
| 5,448,917 A | * | 9/1995 | Maciejewski | 73/812 |
| 7,017,423 B2 | * | 3/2006 | Calloch et al. | 73/849 |
| 7,273,989 B2 | * | 9/2007 | Martin Hernandez et al. | 200/52 R |

* cited by examiner

*Primary Examiner* — Lisa Caputo
*Assistant Examiner* — Octavia Davis-Hollington
(74) *Attorney, Agent, or Firm* — Wenderoth, Lind & Ponack, L.L.P.

(57) ABSTRACT

A device for the fixing of a prismatic mechanical test piece, which consists of two mechanisms that secure the test piece (7) on both sides, where each mechanism consists of two independent blocks (1 and 2), the second block (2) being displaceable in relation to the first (1), at least two rods (3) and a cylinder (4) for assisting the attachment between both blocks (1 and 2), a screw (5) for assuring the attachment between both blocks (1 and 2), and an adapter plate (6) which is adjusted to the second block (2) by means of a pin or bolt (8). Moreover, both blocks (1 and 2) have on the surface facing the test piece (7), an inclined plane (9) which has a grinding at each end in the form of a dovetail (10), such that the test piece (7) remains secured between the two grindings (10).

10 Claims, 3 Drawing Sheets

A-A

DEVICE FOR FIXING OF A PRISMATIC MECHANICAL TEST PIECE, METHOD OF UTILIZATION THEREOF AND USES

OBJECT OF THE INVENTION

As stated in the title of this specification, the present invention relates to providing a device for fixing of a prismatic mechanical test piece. In addition, the present invention has the aim of providing a method of utilization of said device and the specific application to toughness tests on the gluing process, to interlaminar fracture toughness tests, and to toughness tests in mode I, mode II and mixed mode I-II.

TECHNICAL FIELD OF THE INVENTION

The present invention has application in any sector of industry where mechanical tests are required to be conducted on prismatic mechanical test pieces. In particular, it was conceived for the aeronautical industry, more precisely for its use in quality control tests for surface preparation prior to gluing.

STATE OF THE ART PRIOR TO THE INVENTION

In any sector of industry where mechanical tests are required to be conducted on prismatic mechanical test pieces, test pieces are used that consist of two laminas or semi-pieces, stuck together with an adhesive, or test pieces in a single piece are used. It can therefore be said that this concerns prismatic test pieces. For the specific case of toughness tests on the gluing process, test pieces are used consisting of two semi-pieces and for the case of interlaminar fracture toughness tests pieces consisting of a single piece are used. The test pieces consist of a continuous fiber composite material, with the interface of two contiguous layers being tested, or a material that is tested in mode I by means of the test usually known by its initials DCB (Double Cantilever Beam), mode II by means of the test usually known by its initials ELS (End Load Split) and mixed mode I-II by means of the test usually known by its initials MMB (Mixed-Mode Bending) and MMELS (Mixed-Mode End Load Split) [Ref: Robinson, P., Hodgkinson, J. M., (2000). Mechanical Testing of Advanced Fibre Composites. Chapter: Interlaminar fracture toughness. Pages: 170-210. (ed.) Hodgkinson, J. M. Woodhead Publishing: Cambridge (UK)].

For the mechanical fixing of the test pieces for conducting a mechanical test, fixing devices are currently used which require either the use of an adhesive between the fixing device and the specimen or the creation of notches or grindings in the specimen.

The fixing devices that are adhered to the test pieces entail a process that is costly in terms of time and money for preparing the adherence surface. In addition, the reutilization of these devices requires additional tasks of ungluing and treatment or application of a chemical product in order to remove remains of adhesive.

Moreover, with this type of device, misalignments can take place between the fixing device and the specimen. As examples of fixing devices that are adhered to the test pieces, one can cite those known on the market by the name of "hinge".

Although, in the case of fixing devices, notches or grindings are made in the test pieces in order to assure the fixing and avoid treatments prior to reuse and prevent misalignments, they are difficult to adapt to different thickness of specimen and consequently their manufacturer is costly and their reuse is difficult. Also, the notches or grindings made in a specimen can alter its physical properties.

It was therefore desirable to obtain a fixing device for a specimen that would be simple to assemble, easily reusable in test pieces of any thickness, which would also avoid the process of sticking and which would maintain the precision of the test. So, the present invention aims to solve these drawbacks and avoid the type of fixings that require grinding of the test pieces or the use of an adhesive between the specimen and the fixing device.

DESCRIPTION OF THE INVENTION

The present invention relates to providing a device for mechanical fixing of a prismatic specimen for mechanical tests consisting of two mechanisms that secure the specimen on both sides, where each mechanism in turn consists of two independent blocks, the second block moving in relation to the first. The device possesses at least two rods and a cylinder for assisting the attachment between both blocks, in other words, for centering and guiding them. Finally, a screw keeps both blocks attached, said screw also being used for keeping each mechanism fixed to one face of a specimen. Each mechanism also includes an adapter plate. The fixing of the screw is done by means of tightening controlled by a torque screwdriver. In this way, a device is obtained that is easy to set up.

The adapter plate is used for adjusting the device to a test machine external to the device. To achieve this, each adapter plate is adjusted to the set of both blocks already attached by means of a pin or bolt.

Moreover, on the side facing the specimen, each block has an inclined plane terminating at each end with grinding in the form of a dovetail, in such a way that the specimen remains secured between the two grindings.

In this way, the specimen manages to be fixed via its sides. This fixing does not alter its properties when it comes to applying the necessary force for conducting the test. In addition, a device such as that described above is easy and quick to fit and remove and does not require any kind of prior preparation for being used, nor for its reuse.

In order to conduct this type of test, one works with test pieces composed either of two semi-panels stuck together or a block of material composed of continuous fiber, or of an isotropic material that is tested in mode I, or similar.

In a preferred embodiment, for test pieces consisting of a single piece, a groove is made in them or a mold stripper is located in the zone of initiation of the crack, and for test pieces consisting of two semi-panels superimposed and glued a first zone is left without adhesive in order to permit the start of the test. Then, during the course of the test, this initial crack will extend as a reaction to the force exerted, permitting the toughness of the adhesive, or interlaminar fracture toughness, or toughness in mode I, mode II and mixed mode I-II, to be quantified, depending on the test.

In a preferred embodiment, the test pieces have to have a prismatic shape, with a thickness of 3 mm±0.2 mm, a width of 25 mm±1 mm and a length of 250 mm±5 mm. In the event of using test pieces of lesser thickness, a supplement will have to be located.

There are two important dimensions for this device. The angle of incidence of the dovetail grinding and the height thereof. In a preferred embodiment, the height is of 1.3 mm, therefore test pieces of at least 1.5 mm per semi-panel can be used.

In addition, the present invention also describes a preferred manner of utilization for the device for mechanical fixing of a prismatic specimen for mechanical tests described above, which consists of:

having a flat surface for ensuring the perfect alignment between the specimen and both blocks;

lightly fixing the screw joining the blocks of one of the mechanisms to the specimen;

in tests that require this, gently fixing the screw for the blocks of the second mechanism to the specimen;

using the torque screwdriver to tighten the adjusting screws between the blocks in each mechanism. The test pieces therefore remain secured by their sides, thus avoiding the use of adhesives. When the first mechanism is fixed to one of the surfaces of the specimen, this must not be done with the maximum adjustment, instead both mechanisms must first be positioned in order to then apply the final torque setting;

depending on the type of test, securing one or both adapter plates to the test machine for each mechanism, in such a way that the maximum alignment tolerance between both plates is less than 0.3 mm, which will result in a maximum alignment tolerance for the central axes of the adapter plates (6) of less than 1.5 mm;

applying a force to the fixing device, said force is transmitted from a load system external to the fixing device, which can be any of those existing on the market, and regarding which protection is not being applied for, to the adapter plate for each mechanism and via this to the specimen, in order to conduct the test.

Therefore, the device and the method of utilization thereof serves both for tests requiring the fixing of the specimen on both sides by means of two mechanisms per side, and for those requiring the specimen to be fixed on one side only with just one of the mechanisms.

So, a device for mechanical fixing of a prismatic specimen for mechanical tests is achieved which permits the load to be exerted on the central axis of the specimen.

To conclude, the present invention describes some of the more specific uses of the fixing device described above which can be applied to:

a) interlaminar fracture toughness tests on continuous fiber composite material, b) toughness tests in mode I, mode II and mixed mode I-II, on polymer based materials, and c) toughness tests on the gluing process.

The most notable advantages of the device and method described above are:

that it concerns a device that is very economical and simple to construct;

which permits its reuse in successive tests, no matter what the thickness of the specimen to test and without any major prior operations;

which, when the force is applied required for conducting the test, it does not permit any misalignments to occur with the specimen;

which does not require any notches or grinding in the specimen to test, thus avoiding any alterations to the properties of it.

BRIEF DESCRIPTION OF THE FIGURES

The present invention will be entirely understood on the basis of the brief description given below and the accompanying drawings that are presented, solely by way of example and which are therefore not restrictive within the present invention and in which.

REFERENCES

Figure 1:
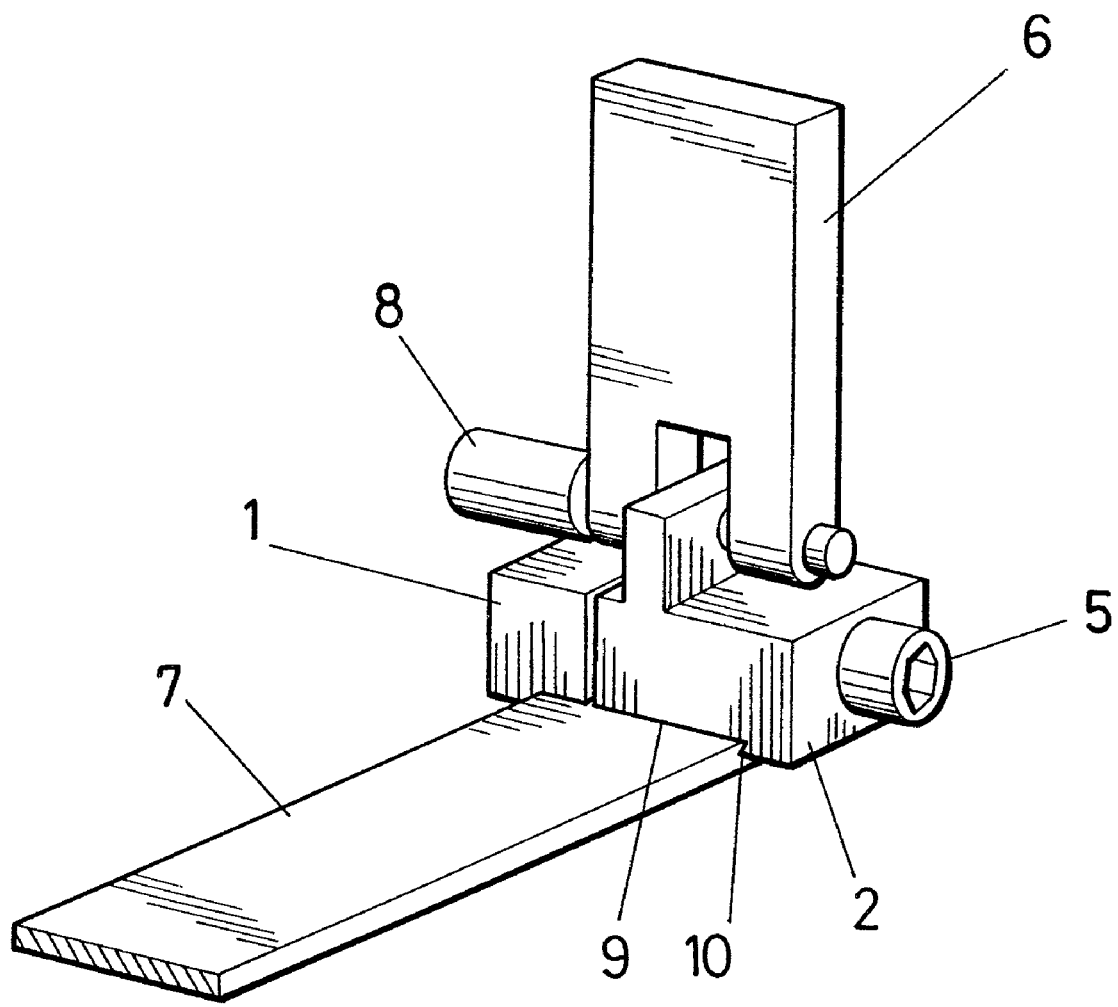
FIG. 1 shows a perspective view of one of the mechanisms mounted on one of the surfaces of the specimen.
Figure 2:
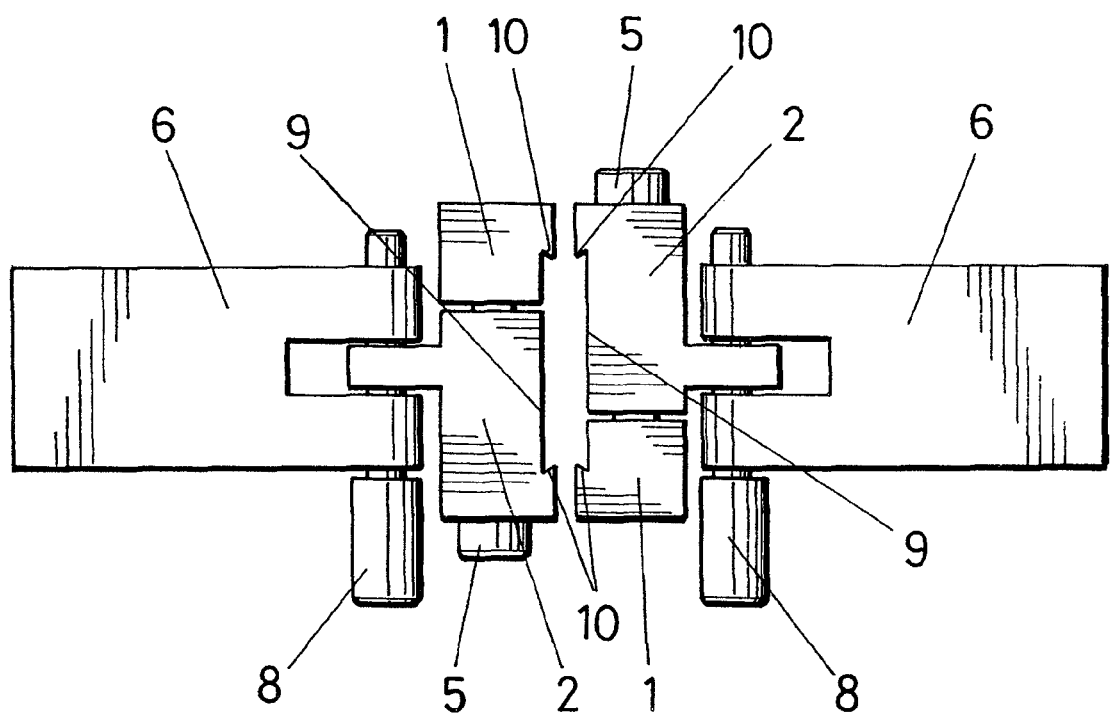
FIG. 2 shows a view of both mechanisms mounted, though without the specimen.

1: fixed block
2: mobile block
3: rods
4: cylinder
5: screw
6: adapter plate to the test machine
7: specimen
8: pin or bolt
9: inclined plane
10: grinding in the form of a dovetail

FORM OF EMBODIMENT OF THE INVENTION

Figure 3:
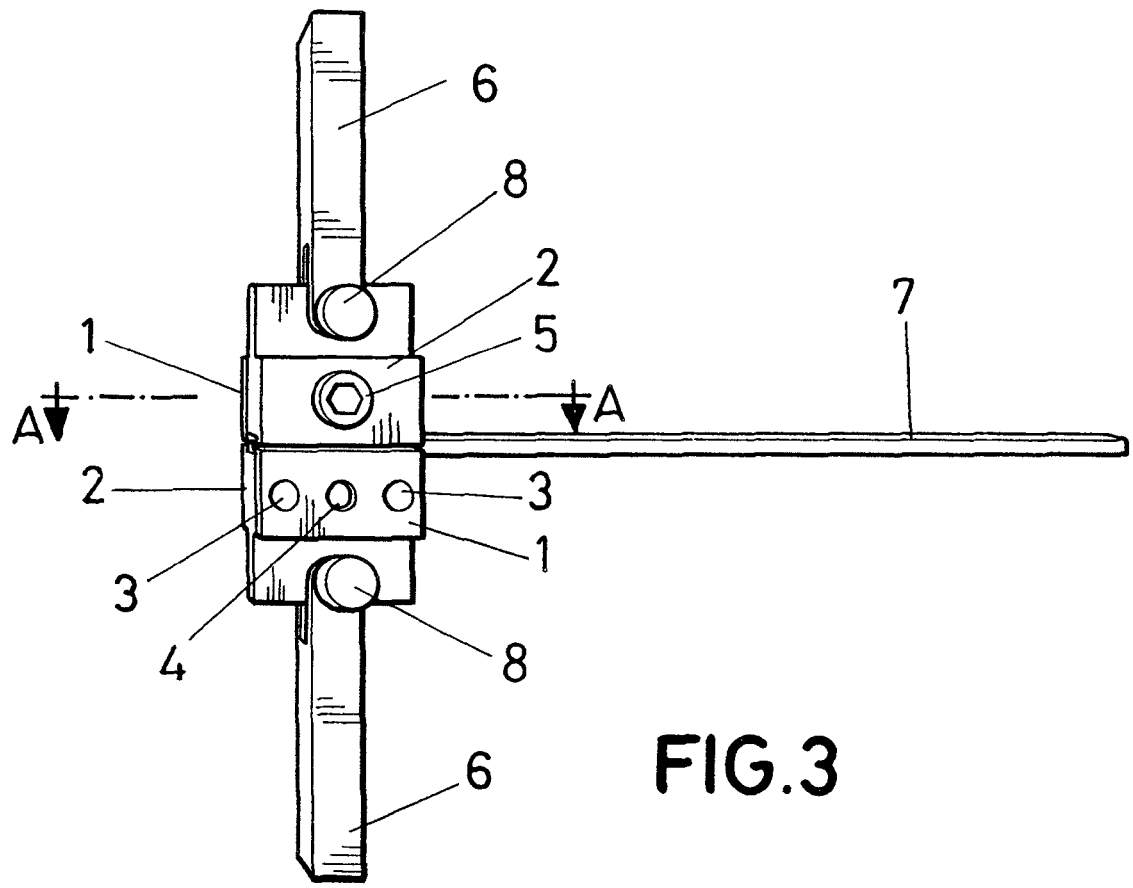
FIG. 3 shows a side view of the device mounted on both surfaces of the specimen.
Figure 4:
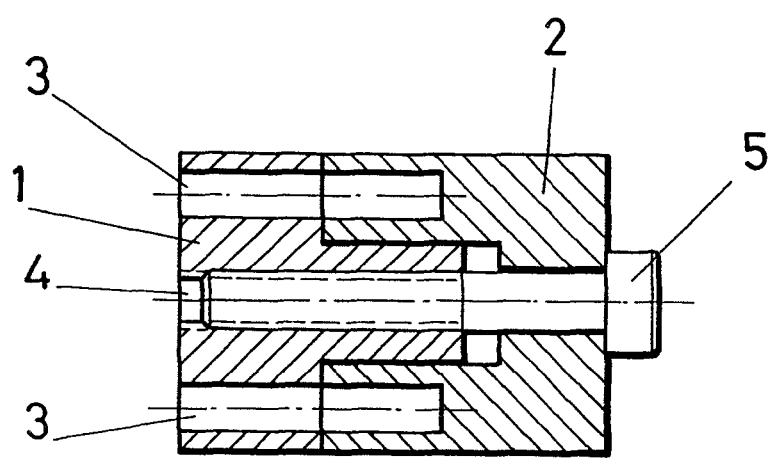
FIG. 4 shows a view along the line of cut A-A of FIG. 1.

With the aim of reaching a better understanding of the object and functionality of this patent, and without being understood as restrictive solutions, so FIG. 3 shows a side view of the device mounted on both surfaces of the specimen (7), which consists of two mechanisms that secure the specimen (7) on both sides, where each mechanism in turn consists of two independent blocks (1 and 2), where the second block (2) moves in relation to the first (1). The device possesses at least two rods (3) and a cylinder (4) for assisting the attachment between both blocks (1 and 2), in other words, for centering and guiding them. Finally, a screw (5) keeps both blocks (1 and 2) attached, said screw (5) also being used for keeping each mechanism fixed to one of the faces of the specimen (7).

The fixing of the screw (5) is done by means of tightening controlled by a torque screwdriver, in this way, a device is obtained that is easy to set up.

In addition, each mechanism possesses an adapter plate (6) used for adjusting the device to a test machine. Each adapter plate (6) is adjusted to each pair of blocks (1 and 2) already attached by means of a pin or bolt (8).

Moreover, on the side facing the specimen (7), each block (1 and 2) has an inclined plane (9) which possesses grinding at each end in the form of a dovetail (10), in such a way that the specimen (7) remains secured between the two grindings (10).

In addition, the present invention describes a preferred manner of utilization for the device for mechanical fixing of a prismatic specimen for mechanical tests described above, which consists of:

having a flat surface for ensuring the perfect alignment between the specimen (7) and both blocks (1 and 2);

lightly fixing the screw (5) joining the blocks (1 and 2) of one of the mechanisms to the specimen (7);

lightly fixing the screw (5) for the blocks (1 and 2) of the second mechanism to the specimen (7);

using the torque screwdriver to tighten the adjusting screw (5) between the blocks (1 and 2) in each mechanism. The test pieces (7) therefore remain secured by their sides, thus avoiding the use of adhesives. When the first mechanism is fixed to one of the surfaces of the specimen, this must not be done with the maximum adjustment, both mechanisms must first be positioned in order to then apply the final torque setting;

securing the adapter plate (6) to the test machine for each mechanism, in such a way that the maximum alignment tolerance between both plates is less than 0.3 mm, which will result in a maximum alignment tolerance for the central axes of the adapter plates (6) of less than 1.5 mm;

applying a force to the fixing device, said force is transmitted from a load system external to the fixing device, which can be any of those existing on the market, and regarding which protection is not being applied for, to the adapter plate (6) for each mechanism and via this to the specimen (7), in order to conduct the test.

The invention claimed is:

1. A device for fixing of a prismatic mechanical test piece, comprising two mechanisms to secure the test piece via its both sides, wherein each mechanism comprises:
    two independent blocks, the second block being displaceable in relation to the first block;
    at least two rods and a cylinder for assisting the attachment between both of the blocks;
    a screw for assuring the attachment between both of the blocks and the test piece; and
    an adapter plate that is fixed to a machine and joined to the second block by a pin or bolt that works as an articulation;
        wherein, for each mechanism, both of the blocks have, on the surface facing the test piece, an inclined plane which includes a grinding at each end in the form of a dovetail, such that the test piece remains secured between the two grindings.

2. Method of utilization of the device for fixing of a prismatic mechanical test piece defined according to claim 1, wherein the method comprises:
    preparing a flat surface for ensuring proper alignment between the test piece and both of the blocks;
    lightly fixing the screw joining the blocks of one of the mechanisms to the test piece;
    lightly fixing the screw for the blocks of the second mechanism to the test piece;
    tightening the screw for the adjustment between the blocks in each mechanism;
    securing the adapter plate for each mechanism with the pin or bolt; and
    applying a force to the fixing device, said force is transmitted from a load system external to the fixing device, to the adapter plate for the device and via this to the test piece.

3. Use of the device for fixing of a prismatic mechanical test piece defined according to claim 2, applied to interlaminar fracture toughness tests on continuous fiber composite materials.

4. Use of the device for fixing of a prismatic mechanical test piece defined according to claim 2, applied to toughness tests in mode I on polymer based materials.

5. Use of the device for fixing of a prismatic mechanical test piece defined according to claim 2, applied to toughness tests on gluing process.

6. Use of the device for fixing of a prismatic mechanical test piece defined according to claim 1, applied to interlaminar fracture toughness tests on continuous fiber composite materials.

7. Use of the device for fixing of a prismatic mechanical test piece defined according to claim 1, applied to toughness tests in mode I on polymer based materials.

8. Use of the device for fixing of a prismatic mechanical test piece defined according to claim 1, applied to toughness tests on gluing process.

9. A device for fixing of a prismatic mechanical test piece, comprising two mechanisms to secure the test piece via its both sides, wherein each mechanism comprises:
    two independent blocks, the second block being displaceable in relation to the first block,
    at least two rods and a cylinder for assisting the attachment between both of the blocks;
    a screw for assuring the attachment between both of the blocks and the test piece; and
    an adapter plate that is fixed to a machine and joined to the second block by a pin or bolt that works as an articulation;
        wherein for each of said two mechanisms, said two independent blocks are disposed adjacent one another so as to form a test piece-receiving surface having a test piece-receiving groove formed therein;
        wherein said test piece-receiving surface of a first of said two mechanisms is configured to face said test piece-receiving surface of a second of said two mechanisms such that said test piece-receiving grooves of said test piece-receiving surfaces are arranged to hold the test piece therein between said two mechanisms; and
        wherein, for each mechanism, both of the blocks have, on the test piece-receiving surface, an inclined plane which includes a grinding at each end in the form of a dovetail, such that the test piece remains secured between the two grindings.

10. Method of utilization of the device for fixing of a prismatic mechanical test piece defined according to claim 9, wherein the method comprises:
    disposing the two mechanisms such that the test piece-receiving surfaces face each other with the test piece-receiving grooves aligned with each other, and disposing the test piece in the test piece-receiving grooves;
    lightly fixing the screw joining the blocks of one of the mechanisms to the test piece;
    lightly fixing the screw for the blocks of the second mechanism to the test piece;
    tightening the screw for the adjustment between the blocks in each mechanism;
    securing the adapter plate for each mechanism with the pin or bolt; and
    applying a force to the fixing device, said force is transmitted from a load system external to the fixing device, to the adapter plate for the device and via this to the test piece.

* * * * *